(12) United States Patent
Emoto et al.

(10) Patent No.: US 9,272,961 B2
(45) Date of Patent: Mar. 1, 2016

(54) PRODUCTION METHOD OF POLYOLEFIN, POLYOLEFIN AND 1-HEXENE FOR LINEAR LOW DENSITY POLYETHYLENE PRODUCTION RAW MATERIAL

(75) Inventors: Hiroki Emoto, Kurashiki (JP);
Kazuyuki Yokoyama, Kurashiki (JP);
Takashi Monoi, Kawasaki (JP);
Kazuhiro Yamamoto, Kawasaki (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 12/521,467

(22) PCT Filed: Nov. 9, 2007

(86) PCT No.: PCT/JP2007/071832
§ 371 (c)(1),
(2), (4) Date: Jun. 26, 2009

(87) PCT Pub. No.: WO2008/078462
PCT Pub. Date: Jul. 3, 2008

(65) Prior Publication Data
US 2010/0331503 A1 Dec. 30, 2010

(30) Foreign Application Priority Data

Dec. 27, 2006 (JP) ................. 2006-351967

(51) Int. Cl.
*C07C 2/02* (2006.01)
*C08F 4/44* (2006.01)
(Continued)

(52) U.S. Cl.
CPC ................. *C07C 2/24* (2013.01); *C07C 11/107* (2013.01); *C08F 210/16* (2013.01); *C08F 4/65908* (2013.01); *C08F 2410/01* (2013.01)

(58) Field of Classification Search
USPC ......... 526/106, 98, 144, 206, 219.4; 502/319, 502/224
See application file for complete search history.

(56) References Cited

U.S. PATENT DOCUMENTS

| 4,406,673 A | 9/1983 | Yamada et al. |
| 5,910,619 A * | 6/1999 | Urata .................. C07C 2/32 585/500 |

(Continued)

FOREIGN PATENT DOCUMENTS

| CN | 1140179 A | 1/1997 |
| EP | 0 699 648 A1 | 3/1996 |

(Continued)

OTHER PUBLICATIONS

U.S. Appl. No. 12/520,096, filed Jun. 19, 2009, Emoto et al.
(Continued)

*Primary Examiner* — David W Wu
*Assistant Examiner* — Elizabeth Eng
(74) *Attorney, Agent, or Firm* — Oblon, McClelland, Maier & Neustadt, L.L.P.

(57) ABSTRACT

The object of the present invention is to provide a production method for a polyolefin, in which catalyst activity is improved, and a polyolefin such as a linear low density polyethylene can advantageously be industrially produced. The present invention relates to a production method for a polyolefin, in which in producing a polyolefin by the polymerization reaction of an olefin using a catalyst, an organohalide is present in the reaction system in an amount of from 0.05 to 10 ppm by weight in terms of the halogen atom as a concentration in a raw material olefin, and 1-hexene for linear low density polyethylene production raw material, containing an organohalide in an amount of from 0.05 to 10 ppm by weight in terms of the halogen atom.

13 Claims, 1 Drawing Sheet

(51) Int. Cl.
  *C08F 210/14* (2006.01)
  *C07C 17/00* (2006.01)
  *C07C 2/24* (2006.01)
  *C07C 11/107* (2006.01)
  *C08F 210/16* (2006.01)
  *C08F 4/659* (2006.01)

(56) References Cited

U.S. PATENT DOCUMENTS

| | | | |
|---|---|---|---|
| 6,133,495 | A | 10/2000 | Urata et al. |
| 6,174,972 | B1 | 1/2001 | Daire |
| 6,479,590 | B1 * | 11/2002 | Ikeda et al. ............ 525/193 |
| 2005/0032993 | A1 | 2/2005 | Yamamoto et al. |

FOREIGN PATENT DOCUMENTS

| | | | |
|---|---|---|---|
| EP | 0 722 955 A1 | 7/1996 | |
| EP | 722955 A1 * | 7/1996 | ............ C08F 10/00 |
| JP | 53 103411 | 9/1978 | |
| JP | 57 183726 | 11/1982 | |
| JP | 63 218707 | 9/1988 | |
| JP | 3 99024 | 4/1991 | |
| JP | 3 234711 | 10/1991 | |
| JP | 5-170828 | 7/1993 | |
| JP | 7-117171 | 5/1995 | |
| JP | 8 134131 | 5/1996 | |
| JP | 8-183747 | 7/1996 | |
| JP | 8 231619 | 9/1996 | |
| JP | 8 283325 | 10/1996 | |
| JP | 9 12627 | 1/1997 | |
| JP | 9 194524 | 7/1997 | |
| JP | 9 268133 | 10/1997 | |
| JP | 9 268135 | 10/1997 | |
| JP | 09268135 A * | 10/1997 | ............ C07C 11/107 |
| JP | 10 36435 | 2/1998 | |
| JP | 10 109946 | 4/1998 | |
| JP | 11 60511 | 3/1999 | |
| JP | 11-80258 | 3/1999 | |
| JP | 2004 182971 | 7/2004 | |
| JP | 2005-306966 | 11/2005 | |
| JP | 2006-143893 | 6/2006 | |

OTHER PUBLICATIONS

U.S. Appl. No. 12/519,778, filed Jun. 18, 2009, Yokoyama et al.
U.S. Appl. No. 12/519,525, filed Jun. 17, 2009, Emoto et al.
Singaporean Written Opinion issued Jun. 13, 2011, in Patent Application No. 200902822-6.
Office Action issued Mar. 3, 2011 in Chinese Patent Application No. 200780044659.5 (with English translation).
Singapore Search Report and Written Opinion issued Aug. 9, 2013 in Patent Application No. 201102979-0.
Canadian Office Action issued Sep. 10, 2013 in Patent Application No. 2,673,907.
Indian Office Action issued Sep. 24, 2014, in India Patent Application No. 4231/DELNP/2009.
Supplementary European Search Report issued Dec. 28, 2011, in European Patent Application No. 070831563.7 filed on Nov. 9, 2007.
Office Action issued Decmeber 19, 2011, in Chinese Patent Application No. 200780044659.5 filed on Nov. 9, 2007 (with English translation).
Office Action issued Feb. 18, 2014 in Indonesian Patent Application No. W00200901804 with English language translation.
Office Action issued May 5, 2014 in Taiwanese Patent Application No. 096149649 with English language translation.
Office Action issued on Jun. 24, 2013 in the corresponding Taiwanese Patent Application No. 096149649 (with English Translation).
Search and Examination Report issued Feb. 29, 2012, in Singapore Patent Application No. 200902822-6, filed Nov. 9, 2007.
Office Action issued Feb. 13, 2014, in Korean Patent Application No. 10-2009-7011365 with English translation.
Japanese Office Action issued Jan. 22, 2013, in Japan Patent Application No. 2007-333927 (with English translation).
Chinese Office Action Issued Oct. 30, 2012 in Chinese Patent Application No. 200780044659.5 (with English translation).
Office Action issued Nov. 30, 2010, in Eurasian Patent Application No. 200970636.
Egyptian Office Action issued Aug. 17, 2010, in Patent Application No. PCT 981/2009 (with English-language translation).
Search Report and Written Opinion issued Oct. 19. 2010 in Singaporean Application No. 2009028226.

* cited by examiner

PRODUCTION METHOD OF POLYOLEFIN, POLYOLEFIN AND 1-HEXENE FOR LINEAR LOW DENSITY POLYETHYLENE PRODUCTION RAW MATERIAL

TECHNICAL FIELD

The present invention relates a production method of a polyolefin, a polyolefin and 1-hexene for linear low density polyethylene production raw material.

BACKGROUND ART

A method of using a catalyst is known as a production method of a polyolefin. For example, where 1-hexene is used as a raw material olefin, a linear low density polyethylene (LLDPE) is obtained.

On the other hand, trimerization reaction of ethylene using a chromium series catalyst is known as a production method of 1-hexene. The representative chromium series catalyst is a chromium series catalyst comprising a combination of at least a chromium compound (a), a nitrogen-containing compound (b), an aluminum-containing compound (c) and a halogen-containing compound (d) (for example, see Patent Document 1).

Trimerization reaction of ethylene is conducted in the presence of a reaction solvent. After completion of the reaction, 1-hexene obtained is treated in a distillation column, and separated and recovered from the reaction solvent. In such a case, 1-hexene may contain a slight amount of an organohalide.

Conventionally, an organohalide in 1-hexene is removed from the fear that the organohalide adversely affects a catalyst for linear low density polyethylene production (single-site catalyst). From long ago, various methods are known as the removal method. For example, a method of using an ion-exchange resin (see Patent Document 2) and a method of using an adsorbent such as alumina, silica, silica-alumina or activated clay (see Patent Document 3) are known. Additionally, a method of using zeolite having a pore size of 5 angstroms or more as an adsorbent is known as a method which is improved so as to remove under mild conditions. By this method, 2-chlorobutane in 1-hexene is removed up to 0.1 ppm by weight or less (0.04 ppm by weight or less in terms of a chlorine atom) (see Patent Document 4).

Patent Document 1: JP-A-11-060511
Patent Document 2: JP-A-53-103411
Patent Document 3: JP-A-57-183726
Patent Document 4: JP-A-3-99024

DISCLOSURE OF THE INVENTION

Problems that the Invention is to Solve

However, according to the finding of the present inventors, surprisingly, an organohalide in 1-hexene does not always adversely affect a catalyst, but in the case of a specific content thereof, the organohalide increases activity of a catalyst. The present invention has been completed based on such a finding. The present invention comprises the related three inventions, and the gist of each invention is described below.

Means for Solving the Problems

Specifically, a first aspect of the present invention resides in a production method of a polyolefin, characterized in that in producing a polyolefin by polymerization reaction of a raw material olefin in the presence of a catalyst, concentration of an organohalide to the raw material olefin is from 0.05 to 10 ppm by weight in terms of a halogen atom.

A second aspect of the present invention resides in a polyolefin, characterized in that it contains an organohalide in an amount of from 0.005 to 1 ppm by weight in terms of a halogen atom, and a third aspect of the present invention resides in 1-hexene for linear low density polyethylene production raw material, characterized in that it contains an organohalide in an amount of from 0.05 to 10 ppm by weight in terms of a halogen atom.

That is, the gist of the present invention resides in the following (1) to (11).

(1) A production method of a polyolefin, characterized in that in producing a polyolefin by polymerization reaction of a raw material olefin in the presence of a catalyst, concentration of an organohalide to the raw material olefin is from 0.05 to 10 ppm by weight in terms of a halogen atom.
(2) The production method as described in (1), wherein 1-hexene is used as the raw material olefin, and the concentration of the organohalide to 1-hexene is from 0.05 to 10 ppm by weight in terms of a halogen atom.
(3) The production method as described in (2), wherein the 1-hexene is obtained by trimerization reaction of ethylene using a chromium series catalyst comprising a combination of a chromium compound (a), a nitrogen-containing compound (b), an aluminum-containing compound (c) and a halogen-containing compound (d).
(4) The production method as described in any one of (1) to (3), wherein the organohalide is an unsaturated organohalide.
(5) The production method as described in (4), wherein the unsaturated organohalide is a halogenated olefin.
(6) A polyolefin, characterized in that it contains an organohalide in an amount of from 0.005 to 1 ppm by weight in terms of a halogen atom.
(7) The polyolefin as described in (6), which is a linear low density polyethylene.
(8) 1-Hexene for linear low density polyethylene production raw material, characterized in that it contains an organohalide in an amount of from 0.05 to 10 ppm by weight in terms of a halogen atom.
(9) The 1-hexene as described in (8), wherein the 1-hexene is obtained by trimerization reaction of ethylene using a chromium series catalyst comprising a combination of a chromium compound (a), a nitrogen-containing compound (b), an aluminum-containing compound (c) and a halogen-containing compound (d).
(10) The 1-hexene as described in (8) or (9), wherein the organohalide contained in 1-hexene is an unsaturated organohalide.
(11) The 1-hexene as described in (10), wherein the organohalide is a halogenated olefin.

Advantage of the Invention

According to the present invention, catalyst activity is increased, and a polyolefin such as a linear low density polyethylene can be produced industrially advantageously.

DESCRIPTION OF REFERENCE NUMERALS AND SIGNS

10: Completely mixing and stirring type reactor
11: Deactivator supply piping

12: First supply piping
12a: Ethylene supply piping
13: Second supply piping
13a: Catalyst supply piping
14: Third supply piping
15: Fourth supply piping
16: Compressor
20: Degassing tank
30: Ethylene separation column
40: High boiling separation column
50: Hexene separation column
70: Solvent drum

BEST MODE FOR CARRYING OUT THE INVENTION

The present invention is described in detail below.

In the production method of an α-olefin low polymer to which the embodiment of the invention is applied, the α-olefin used as a raw material includes substituted or unsubstituted α-olefins having from 2 to 30 carbon atoms. Specific examples of such an α-olefin include ethylene, propylene, 1-butene, 1-hexene, 1-octene, 3-methyl-1-butene and 4-methyl-1-pentene. In particular, ethylene is preferred as the α-olefin of a raw material, and when ethylene is used as the raw material, 1-hexene as a trimer of ethylene is obtained in high yield and high selectivity. Furthermore, when ethylene is used as the raw material, impurity components other than ethylene may be contained in the raw material. Specific impurity components include methane, ethane, acetylene and carbon dioxide. Those components are preferably in an amount of 0.1 mol % or less based on ethylene of the raw material.

In the following description, 1-hexene for linear low density polyethylene production raw material is described for the sake of convenience of the description.

1-Hexene of the present invention is obtained by trimerization reaction of ethylene using a chromium series catalyst. The trimerization reaction of ethylene is basically conducted according to the method described in, for example, JP-A-11-060511.

The chromium series catalyst comprises a combination of at least a chromium compound (a), a nitrogen-containing compound (b) and an aluminum-containing compound (c). According to need, the chromium series catalyst further containing a halogen-containing compound (d) is used.

The chromium compound (a) includes at least one compound represented by the general formula $CrX_n$. In the general formula, X represents an optional organic group, inorganic group or negative atom, and n is an integer of from 1 to 6, and is preferably 2 or more. When n is 2 or more, Xs may be the same or different.

Examples of the organic group include a hydrocarbon group having from 1 to 30 carbon atoms, a carbonyl group, an alkoxy group, a carboxyl group, a β-diketonate group, a β-ketocarboxyl group, a β-ketoester group and an amido group. Examples of the inorganic group include chromium salt-forming groups such as a nitric acid group or a sulfuric acid group. Examples of the negative atom include oxygen and a halogen. A halogen-containing chromium compound is not included in the halogen-containing compound (d) described hereinafter.

The number of valency of chromium (Cr) is 0 to 6. The preferred chromium compound (a) includes a carboxylate of chromium (Cr). Specific examples of the carboxylate of chromium include chromium (II) acetate, chromium (III) acetate, chromium (III)-n-octanoate, chromium (III)-2-ethylhexanoate, chromium (III) benzoate and chromium (III) naphthenate. Of those, chromium (III)-2-ethylhexanoate is particularly preferred.

The nitrogen-containing compound (b) includes at least one compound selected from the group consisting of an amine, an amide and an imide. Examples of the amine include a primary amine compound, a secondary amine compound and a mixture of those. Examples of the amide include a metal amide compound derived from a primary amine compound or a secondary amide compound, a mixture of those, and an acid amide compound. Of those, a secondary amine compound is preferred.

Specific examples of the secondary amine compound include pyrroles such as pyrrole, 2,4-dimethylpyrrole, 2,5-dimethylpyrrole, 2-methyl-5-ethylpyrrole, 2,5-dimethyl-3-ethylpyrrole, 3,4-dimethylpyrrole, 3,4-dichloropyrrole, 2,3,4,5-tetrachloropyrrole, 2-acetyl-pyrrole and dipyrrole comprising two pyrrole rings bonded through a substituent, and their derivatives. Examples of the derivative include metal pyrrolide derivatives. Specific examples of the metal pyrrolide derivative include diethylaluminum pyrrolide, ethylaluminum dipyrrolide, aluminum tripyrrolide, sodium pyrrolide, lithium pyrrolide, potassium pyrrolide, diethylaluminum(2,5-dimethylpyrrolide), ethylaluminum bis(2,5-dimethylpyrrolide), aluminum tris(2,5-dimethylpyrrolide), sodium(2,5-dimethylpyrrolide), lithium(2,5-dimethylpyrrolide) and potassium(2,5-dimethylpyrrolide). Of those, 2,5-dimethylpyrrole and diethylaluminum(2,5-dimethylpyrrolide) are preferred. (Here, the aluminum pyrrolides are not included in the aluminum-containing compound (c). Furthermore, the halogen-containing pyrrole compound (b) is not included in the halogen-containing compound (d).)

The aluminum-containing compound (c) includes at least one compound such as a trialkylaluminum compound, an alkoxyalkylaluminum compound and a hydrogenated alkylaluminum compound. Specific examples thereof include trimethylaluminum, triethylaluminum, triisobutylaluminum, diethylaluminum ethoxide and diethylaluminum hydride. Of those, triethylaluminum is particularly preferred.

Examples of the halogen-containing compound (d) include at least one compound of a halogenated alkylaluminum compound, a linear halohydrocarbon with 2 or more carbon atoms, having 3 or more halogen atoms and a cyclic halohydrocarbon with 3 or more carbon atoms, having 3 or more halogen atoms. (The halogenated alkylaluminum compound is not included in the aluminum-containing compound (c)). Specific examples of the halogen-containing compound (d) include diethylaluminum chloride, ethylaluminum sesquichloride, carbon tetrachloride, 1,1,1-trichloroethane, 1,1,2,2-tetrachloroethane, pentachloro-ethane, hexachloroethane, 1,2,3-trichlorocyclopropane, 1,2,3,4,5,6-hexachlorocyclohexane and 1,4-bis(trichloro-methyl)-2,3,5,6-tetrachlorobenzene.

The trimerization reaction of ethylene is conducted in the presence of a reaction solvent. Examples of the reaction solvent used include chain saturated hydrocarbons or alicyclic saturated hydrocarbons, having from 1 to 20 carbon atoms, such as butane, pentane, 3-methylpentane, hexane, heptane, 2-methylhexane, octane, cyclohexane, methylcyclohexane, 2,2,4-trimethylpentane and decalin; and aromatic hydrocarbons such as benzene, toluene, xylene, ethylbenzene, mesitylene and tetralin. Furthermore, 1-hexene formed by trimerization of ethylene may be used as a solvent. Those can be used as a mixed solvent of two or more thereof. The particularly preferred solvent is chain saturated hydrocarbons or alicyclic saturated hydrocarbons, having from 4 to 10 carbon atoms. When those solvents are used, by-produced polymers such as a polyethylene can be suppressed. Furthermore, when the alicyclic saturated hydrocarbons are used, high catalyst activity tends to be obtained.

The amount of the chromium compound used is generally from $1.0 \times 10^{-7}$ to 0.5 mole, preferably from $5.0 \times 10^{-7}$ to 0.2 mole, and more preferably from $1.0 \times 10^{-6}$ to 0.05 mole, per 1 liter of a solvent described hereinafter, in terms of the amount per chromium atom of the chromium compound (a). By using such a chromium series catalyst, for example, when ethylene is used as the raw material, hexene which is a trimer of ethylene can be obtained in selectivity of 90% or more. Furthermore, in this case, the proportion of 1-hexene occupied in hexene can be 99% or more.

The molar ratio (a):(b):(c):(d) of the chromium compound (a), the nitrogen-containing compound (b), the aluminum-containing compound (c) and the halogen-containing compound (d) is generally 1:(1 to 50):(1 to 200):(1 to 50), and preferably 1:(1 to 30):(10 to 150):(1 to 30). By the combination of such specific conditions, hexene can be produced in yield of 90% or more (proportion to the total formation amount), and purity of 1-hexene in hexene can be increased to 99% or higher.

Molar ratio of 1-hexene to ethylene in a reaction liquid in trimerization reaction of ethylene ((1-hexene in reaction liquid)/(ethylene in reaction liquid)) is generally from 0.05 to 1.5, and preferably from 0.10 to 1.0. It is preferred that in the case of a continuous reaction, catalyst concentration, reaction pressure and other conditions are adjusted such that the molar ratio of ethylene and 1-hexene in the reaction liquid is fallen within the above range, and in the case of a batch reaction, the reaction is stopped at the time that the molar ratio is fallen within the above range. By this, there is the tendency that by-production of components having a boiling point higher than that of 1-hexene is suppressed, and selectivity of 1-hexene is further increased.

The reaction temperature is in a range of generally from 0 to 250° C., preferably from 50 to 200° C., and further preferably from 80 to 170° C. On the other hand, the reaction pressure can be selected from a range of from ordinary pressures to 250 kgf/cm², but in general, pressure of 100 kgf/cm² is sufficient. The reaction time is in a range of generally from 1 minute to 20 hours, and preferably from 0.5 to 6 hours. The reaction format may be any of a batch method, a semi-batch method and a continuous method. After completion of the reaction, the reaction liquid is treated in a distillation column and separated into an α-olefin mainly comprising 1-hexene and a reaction solvent. A slight amount of α-olefin is C4 component, C6 component other than 1-hexene, C8 component, C10 component, C14 component and the like.

1-Hexene of the present invention is characterized by containing an organohalide in an amount of from 0.05 to 10 ppm by weight in terms of a halogen atom. In the production of 1-hexene, the 1-hexene of the present invention can be obtained by remaining a slight amount of an organohalide contained in 1-hexene without removal of an organohalide that is conducted to 1-hexene (the above-described α-olefin) separated and recovered form the reaction solvent. Furthermore, from the standpoint of controlling the content of an organohalide, a method may be employed that after removal of an organohalide, a constant amount of an organohalide is added to 1-hexene recovered.

Examples of the organohalide contained in 1-hexene of the present invention include organohalides by-produced by decomposition product of the halogen-containing compound (d) used as a component of the chromium series catalyst, and/or organohalides by-produced by that halogen atoms generated from the halogen-containing compound (d) is substitution reacted with hydrogen atoms of a raw material ethylene. Examples of those by-produced organohalides include monochloromethane, monochloroethane, monochloroethylene, 1,1-dichloroethylene, 1,2-dichloroethylene (cis- and trans-forms), trichloro-ethylene, tetrachloroethylene, allyl chloride and 3,3-dichloro-1-propene. The organohalide contained in 1-hexene of the present invention is an organohalide that a chlorine atom is difficult to be pulled out by a single-site catalyst for polyolefin production, preferably an unsaturated organohalide, and further preferably the halogenated olefin described above as a by-produced organohalide. The halogenated olefin generally has a boiling point of 150° C. or lower, and is therefore difficult to separate from 1-hexene by distillation.

The amount of the organohalide contained in 1-hexene of the present invention is from 0.05 to 10 ppm by weight, preferably from 0.1 to 10 ppm by weight, and more preferably from 0.5 to 10 ppm by weight, in terms of a halogen atom. Where the content of the organohalide is too small, the effect of increasing activity of a single-site catalyst is not sufficiently exhibited, and where the amount is too large, the organohalide may act as a poisoning substance to a single-site catalyst.

The production method of a polyolefin according to the present invention is described below. In the present invention, a polyolefin is produced by polymerization reaction of an olefin using a catalyst. The catalyst is preferably a single-site catalyst.

The single-site catalyst can use the conventional catalysts without limitation. For example, a catalyst (metallocene catalyst) comprising a metallocene complex (component A), a co-catalyst (component B) and if necessary, an organoaluminum compound (component C) can be used. Depending on characteristics of olefin polymerization process, a carrier (component D) may further be used as a constituent for particulation.

The metallocene complex includes metallocene complexes of transition metal compounds of groups 4 to 6 in a periodic table (short period type, hereinafter the same), having a conjugated five-membered ring ligand. Of those, complexes represented by the following general formula (1) or (2) are preferred.

[Chem. 1]

(1)

(2)

In the general formula (1) or (2), A and A' represent a cyclopentadienyl group which may have a substituent. Example of the substituent includes a hydrocarbon group having from 1 to 30 carbon atoms. The hydrocarbon group may be bonded as a monovalent group to the cyclopentadienyl group, and when plural hydrocarbon groups are present, two of those groups may be bonded at the respective other end (ω-end) to form a ring together with a part of cyclopentadienyl. Other examples of the substituent include an indenyl group, a fluorenyl group and an azrenyl group. Those groups may further have a substituent on a sub-ring. Of those, an indenyl group and an azrenyl group are preferred.

Q represents a bonding group which crosslinks two conjugated five-membered ring ligands at an arbitrary position, and specific examples thereof include an alkylene group, a silylene group and a germylene group. Those groups may further have a substituent.

M represents a metal atom of a transition metal selected from groups 4 to 6 of the periodic table, and examples thereof include titanium, zirconium and hafnium. Of those, zirconium or hafnium is preferred.

X and Y are an auxiliary ligand, and react with the component (B) to form an active metallocene having olefin polymerizability. Therefore, the kind of X and Y is not limited so long as this object is achieved. Specific examples of X and Y each represents a hydrogen atom, a halogen atom, a hydrocarbon group, and a hydrocarbon group which may have a hetero atom. Of those, a hydrocarbon group having from 1 to 10 carbon atoms or a halogen atom is preferred.

The promoter (activating agent component) is a component which activates a metallocene complex, and is a compound which reacts with an auxiliary ligand of a metallocene complex and can convert the metallocene complex into an active species having an olefin polymerizability. Specific examples of the promoter include the following (B-1) to (B-4).

(B-1): Aluminumoxy compound
(B-2): Ionic compound or Lewis acid, that reacts with the component (A) and can convert the component (A) into a cation.
(B-3): Solid acid
(B-4): Ion-exchangeable laminar silicate Regarding the aluminumoxy compound, it is well known that the aluminumoxy compound can activate a metallocene complex, and specific examples thereof include compounds represented by the following general formulae (3) to (5).

[Chem. 2]

(3)

(4)

(5)

In the above each formula, $R^1$ represents a hydrogen atom or a hydrocarbon residue, preferably a hydrocarbon residue having from 1 to 10 carbon atoms, and particularly preferably a hydrocarbon residue having from 1 to 6 carbon atoms. $R^1$s may be the same or different. p is an integer of from 0 to 40, and preferably from 2 to 30.

The compounds represented by the general formulae (3) and (4) are a compound called aluminoxane. Of those, methyl aluminoxane or methyl isobutyl aluminoxane is preferred. The aluminoxane can be used as a mixture in each group and among groups. The aluminoxane can be prepared under the conventional various conditions.

The compound represented by the general formula (5) can be obtained by the reaction between one kind of a trialkyl aluminum or two kinds or more of a trialkyl aluminum, and an alkylboronic acid represented by the general formula $R^2B(OH)_2$ in 10:1 to 1:1 (molar ratio).

Examples of the ionic compound or Lewis acidic compound, which reacts with the component (A) and can convert the component (A) into a cation include compounds in which a cation such as a carbonium cation or an ammonium cation, and an anion such as tetraphenyl borate, tetrakis(3,5-difluorophenyl)borate, tetrakis(pentafluorophenyl)borate or tetrakis(phentafluorophenyl)aluminate form an ion pair.

Examples of the Lewis acidic compound include various organoboron compounds such as tris(penta-fluorophenyl)borate. The organoboron compound used herein encompasses an ionic compound in which an organoboron compound is present as a part of ion pair. Examples other than the above include metal halides such as aluminum chloride and magnesium chloride.

A certain kind of the Lewis acidic compound can be recognized as an ionic compound which reacts with the component (A) and can convert the component (A) into a cation.

Metallocene catalysts using the above-described non-coordinating boron compound are illustrated in, for example, JP-A-3-234709 and JP-A-5-247128.

Specific examples of the organoboron compound include at least one compound of compounds represented by the following general formula (6) that is a Lewis acidic compound and represented by the following formula (7) that is an ionic compound.

[Chem. 3]

$$BR^3R^4R^5 \qquad (6)$$

(In the formula, $R^3$ to $R^5$ which may be the same or different each represents a $C_1$ to $C_{14}$ hydrocarbon containing a halogenated aryl group or a halogenated aryloxy group.

[Chem. 4]

$$A(BR^6R^7R^8R^9)_n \qquad (7)$$

(In the formula, A represents an amine or ammonium salt, a carbocation or a metal cation of valency of +1 to +4, $R^6$ to $R^9$ which may be the same or different each represents a $C_1$ to $C_{14}$ hydrocarbon group containing a halogenated aryl group or a halogenated alkyl group, and n is an integer of from 1 to 4.)

As the specific examples of the hydrocarbon groups of the general formulae (6) and (7), a pentafluorophenyl group, a pentafluorobenzyl group, tetrafluorophenyl group and a tetrafluorotolyl group are preferred. As the specific examples of A in the general formula (7), N,N-dimethylanilinium or triphenylmethyl is preferred.

Examples of the solid acid include alumina, silica-alumina and silica-magnesia.

The ion-exchangeable laminar compound occupies a major portion of a clay mineral, and is preferably an ion-exchangeable laminar silicate. The ion-changeable laminar silicate (hereinafter sometimes simply abbreviated as "silicate") has a crystal structure that faces constituted of ion bond or the like are mutually piled in parallel by bonding force, and means a silicate compound that an ion contained is exchangeable. Most silicates are naturally produced as mainly a main component of a clay mineral, and therefore frequently contain foreign substances (quartz, cristobalite and the like) other than the ion-exchangeable laminar silicate, but those may be contained. Conventional various silicates can be used as the silicate. Specifically, the following laminar silicates described in Haruo Shiromizu, *Nendo Kobutsu Gaku* (Clay Mineralogy), Asakura Publishing Co., Ltd. (1995) are illustrated.

Examples of 2:1 type minerals include smectite group minerals such as montmorillonite, sauconite, beidellite, nontronite, saponite, hectorite and stevensite; vermiculite group minerals such as vermiculite; mica group minerals such as mica, illite, sericite or glauconite; pyrophyllite-talc group minerals such as pyrophyllite or talc; and chlorite group minerals such as Mg chlorite. Examples of 2:1 ribbon type minerals include sepiolite and palygorskite.

The silicate may be a laminar silicate in which the above mixed layer is formed. The silicate as the main component is preferably a silicate having 2:1 type structure, more preferably smectite group, and particularly preferably montmorillonite.

The silicate obtained as a natural product or an industrial raw material can directly be used without particular treatment, but is preferably subjected to a chemical treatment. Specific examples of the chemical treatment include an acid treatment, an alkali treatment, a salt treatment and an organic treatment. Those treatment conditions are not particularly limited, and can use the conventional conditions. In general, the ion-exchangeable laminar silicate contains adsorbed water and interlaminar water, and is therefore preferably used after removing water by applying, for example, heat dehydration treatment under inert gas flow.

The organoaluminum compound used according to need is an organoaluminum compound which does not contain a halogen. The organoaluminum compound is preferably compounds represented by the following general formula (8). The compounds illustrated as the aluminumoxy compound in the promoter described above can also be used.

[Chem. 5]

$$AlR_{3-i}X_i \qquad (8)$$

(In the formula, R represents a hydrocarbon group having from 1 to 20 carbon atoms, X represents a hydrogen atom, an alkoxy group, a phenoxy group, a siloxy group or an amino group, and i is a number of $0 \le i < 3$, provided that when X is hydrogen, i is $0 < i < 3$.)

Specific examples of the organoaluminum compound include trialkyl aluminum such as trimethyl aluminum, triethyl aluminum, tripropyl aluminum, triisobutyl aluminum and trioctyl aluminum; alkoxy-containing alkyl aluminum such as dimethyl aluminum methoxide, diethyl aluminum methoxide, diisobutyl aluminum methoxide, and diisobutyl aluminum ethoxide; phenoxy-containing aluminum such as dimethyl aluminum phenoxide; siloxy-containing aluminum such as dimethyl aluminum trimethyl siloxide and dimethyl aluminum triphenyl siloxide; amino-containing alkyl aluminum such as (diethylamino)diethyl aluminum and di(diethylamino)ethyl aluminum; and halide-containing alkyl aluminum such as diethyl aluminum halide. Of those, trialkyl aluminum is preferred, and trimethyl aluminum, triethyl aluminum, triisobutyl aluminum or trioctyl aluminum is more preferred.

The component (A) and the component (B) are used in an optimum amount ratio in the respective combinations. When the component (B) is an aluminumoxy compound, the molar ratio of Al/transition metal is in a range of generally from 10 to 100,000, preferably from 100 to 20,000, and more preferably from 100 to 10,000. On the other hand, when an ionic compound or Lewis acid is used as the component (B), the molar ratio of transition metal is in a range of generally from 0.1 to 1,000, preferably from 0.5 to 100, and more preferably from 1 to 50. When a solid acid or an ion-exchangeable laminar silicate is used as the component (B), the amount of a transition metal complex used is in a range of generally from 0.001 to 10 mmol, and preferably from 0.001 to 1 mmol, per 1 g of the component (B).

Before a catalyst for olefin production comprising a transition metal and a promoter is used as a catalyst for olefin polymerization (main polymerization), the catalyst is supported on a carrier according to need, and such a catalyst may be subjected to a pre-polymerization treatment which preliminarily polymerizes a small amount of an olefin. The pre-polymerization method can use the conventional methods.

Examples of the raw material olefin include ethylene, propylene, 1-butene, 1-hexene, 1-octene, 4-methyl-1-pentene, 3-methyl-1-butene, vinyl cycloalkane and styrene. The polymerization can suitably apply random copolymerization and block copolymerization as well as homopolymerization. Ethylene is general as a comonomer in the case of the copolymerization.

Examples of the polymerization reaction format include a slurry polymerization and a solution polymerization, conducting in the presence of an inert hydrocarbon solvent such as butane, pentane, hexane, heptane, toluene and cyclohexane; a bulk polymerization conducting in the presence of a solvent such as liquefied α-olefin; a high pressure ion polymerization conducting under critical condition of α-olefin; and a gas phase polymerization in the state that a liquid phase such as a solvent or a monomer is not substantially present. The gas phase polymerization can be conducted using a reaction apparatus such as a fluidized bed, a stirring bed and a stirring fluidized bed equipped with a stirring and mixing machine. The polymerization temperature is generally from −50 to 350° C., and preferably from 0 to 300° C. The polymerization pressure is in a range of generally from ordinary pressures to about 2,000 kgf/cm², preferably from ordinary pressures to 1,500 kgf/cm², and more preferably from ordinary pressures to 1,300 kgf/cm². Hydrogen may be present as a molecular weight modifier in the polymerization reaction system.

The greatest characteristic of the present invention resides in that in producing a polyolefin by polymerization reaction of an olefin using a catalyst, an organohalide is present in a polymerization reaction system in an amount of from 0.05 to 10 ppm by weight in terms of a halogen atom as a concentration of a raw material olefin. The concentration of the organohalide is preferably from 0.1 to 10 ppm by weight, and more preferably from 0.5 to 10 ppm by weight.

Specific examples of the organohalide include organohalides as described in 1-hexene of the present invention. Of those, an unsaturated organohalide is preferred, and a halogenated olefin is more preferred.

When the organohalide is, for example, a chlorination product, an analysis of chlorine concentration in 1-hexene can be conducted under the following conditions using a gas chromatography equipped with an atomic emission detector (AED/GC).

Analyzer: Gas chromatography (Agilent 6890)
    Atomic emission detector (chlorine atom)
    Agilent G2350A (Cl 479 nm)
    Supelcowax-10, strong polarity, 0.32 mm, 60 m, 0.25 μm
Measurement conditions: Gas He=40 cm/s
    Injection temperature 250° C.
    Column temperature 50° C.→200° C., 10° C./min
    Calibration for quantitatively determining chlorine concentration can be conducted with a make-up liquid of, for example, trichloroethylene.

When a linear low density polyethylene is produced using 1-hexene of the present invention as a raw material olefin of polymerization reaction of an olefin using a single-site catalyst, the following embodiments are illustrated.

(1) A production method of a linear low density polyethylene, comprising obtaining 1-hexene by trimerization reaction of ethylene using a chromium series catalyst, and without removal of an organohalide, polymerizing 1-hexene containing the organohalide in an amount of from 0.05 to 10 ppm by weight in terms of a halogen atom in the presence of a single-site catalyst.

(2) A production method of a linear low density polyethylene, comprising obtaining 1-hexene by trimerization reaction of ethylene using a chromium series catalyst, removing an organohalide, adding an organohalide to 1-hexene so as to be a concentration of from 0.05 to 10 ppm by weight in terms of a halogen atom, and polymerizing it in the presence of a single-site catalyst.

In the present invention, the organohalide can be added to a polymerization reaction system of a single-site catalyst. When the raw material olefin does not contain an organohalide, the organohalide may be added to the raw material olefin, and may be added to a polymerization reaction system separately from the raw material olefin. For example, the organohalide can be added together with hydrogen used as a molecular weight modifier.

The polyolefin of the present invention is described below. The polyolefin of the present invention is obtained by polymerizing in the presence of a given amount of an organohalide as described above, and is characterized in that the organohalide is contained in an amount of from 0.005 to 1 ppm by weight in terms of a halogen atom. The preferred concentration of the organohalide in a polyolefin is from 0.005 to 0.5 ppm by weight. The preferred polyolefin in the present invention is a linear low density polyethylene.

The present invention is described further specifically based on the Examples. However, the present invention is not limited to the following Examples so far as it does not depart from its gist. In the following Examples, a linear low density polyethylene was produced from 1-hexene.

Reference Example 1

Production of 1-Hexene by Continuous Process

Figure 1:
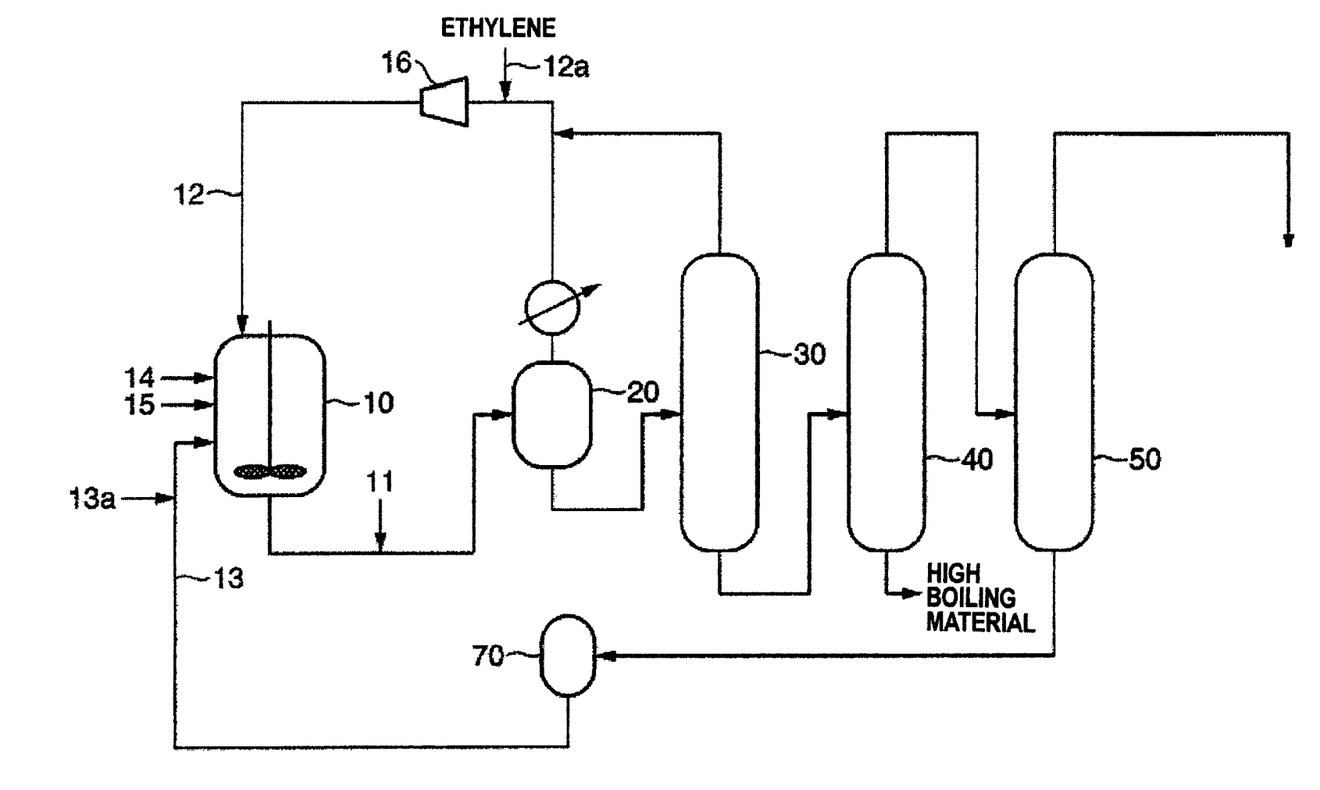
FIG. 1 is an explanatory view of a production process of 1-hexene used in Reference Example 1.

The representative example of producing 1-hexene by a continuous reaction process is shown in FIG. 1. In a process having a completely mixing and stirring type reactor 10, a degassing tank 20, an ethylene separation column 30, a high boiling separation column 40, a hexene separation column 50 and a solvent drum 70 which stores a circulation solvent as shown in FIG. 1, continuous low polymerization reaction of ethylene is conducted to produce 1-hexene.

Unreacted ethylene separated from the degassing tank 20 and the ethylene separation column 30 is continuously supplied together with ethylene freshly supplied from an ethylene supply piping 12a to the reactor 10 from a first supply piping 12 by a compressor 16. A recovered n-heptane solvent separated in the hexene separation column 50 is passed through the solvent drum 70, and is continuously supplied to the reactor 10 from a second supply piping 13 at a flow rate of 40 liters/hr.

Next, an n-heptane solution containing chromium (III) 2-ethylhexanoate (a) and 2,5-dimethylpyrrole (b) is supplied from a catalyst supply piping 13a at a flow rate of 0.1 liter/hr, and is continuously supplied to the reactor 10 via the second supply piping 13. An n-heptane solution of triethylaluminum (c) is continuously supplied to the reactor 10 from a third supply piping 14 at a flow rate of 0.03 liter/hr. Furthermore, an n-heptane solution of hexachloroethane (d) is continuously supplied to the reactor 10 from a fourth supply piping 15 at a flow rate of 0.02 liter/hr. A catalyst is continuously supplied to the reactor 10 such that the molar ratio of each component is (a):(b):(c):(d)=1:6:60:6. The reaction conditions are 120° C. and 51 kgf/cm$^2$.

2-Ethylhexanol as a metal solubilizing agent is added to a reaction liquid continuously withdrawn from the reactor 10 from a deactivator supply piping 11 at a flow rate of 0.005 liter/hr, and such a reaction liquid is then successively treated in the degassing tank 20, the ethylene separation column 30, the high boiling separation column 40 and the hexene separation column 50. As a result, 1-hexene can be obtained from the top of the hexene separation column 50.

Reference Example 2

Production of 1-Hexene by Batch Process

A 2 liters autoclave dried in a dryer at 150° C. was assembled in heating, and was vacuum substituted with nitrogen. A catalyst feed pipe equipped with a rupture disk was fitted to the autoclave. 750 ml of an n-heptane solution containing 26.6 mg (0.280 mmol) of 2,5-dimethylpyrrole, 320 mg (2.80 mmol) of triethylaluminum and 66.4 mg (0.280 mmol) of hexachloroethane was charged in the autoclave. 3 ml of an n-heptane solution containing 22.5 mg (0.0467 mmol) of chromium (III)-2-ethylhexanoate was charged in the catalyst feed pipe. The autoclave was heated to 120° C., and ethylene was introduced into the catalyst feed pipe. The rupture disk was ruptured by ethylene pressure, and ethylene and chromium (III)-2-ethylhexanoate were introduced into the autoclave, thereby low polymerization of ethylene was initiated. Ethylene was introduced until the total pressure reaches 51 kgf/cm$^2$. Thereafter, the total pressure was maintained at 51 kgf/cm$^2$ and the reaction temperature was maintained at 120° C. One hour later, 1.46 g (11.2 mmol) of 2-ethylhexanol was introduced into the autoclave, and the reaction was stopped. Thereafter, the temperature of the reaction liquid was lowered to 40° C., and ethylene was discharged to obtain a reaction liquid. The whole amount of the reaction liquid obtained was charged in a pot of Oldershaw distillation apparatus having 20 actual plates, distillation was conducted at a reflux ratio of 3 at ordinary pressures, and 1-hexene was distilled from the top. When the top temperature was higher than the boiling point of 1-hexene, distillation of 1-hexene from the top was stopped.

Halogen atom concentration in 1-hexene was measured in the following manner. That is, 100 ml of 1-hexene and 20 ml of an NaOH aqueous solution (20 wt %) were placed in a separatory funnel, and the separatory funnel was set to a shaker, and shaken for 1 hour. 15 ml of the NaOH aqueous solution was collected, and neutralized with a nitric acid aqueous solution. Analysis was conducted with an ion chromatography under the following measurement conditions. As a result, chlorides (in terms of a chlorine atom) in 1-hexene distilled from the top in Reference Example 2 were 1 ppm by weight.

As a result of measurement with a gas chromatograph-mass spectrometer (GC-MS) in order to identify a structure of the chlorides, organochlorides such as tetrachloroethylene, trichloroethylene and cis-1,2-dischloroethylene were contained in 1-hexene.

<Analysis of Commercially Available 1-Hexene>

On the other hand, when a halide (in terms of a halogen atom) in the commercially available 1-hexene (a product of Mitsubishi Chemical Corporation, Dialen 6) was measured, the amount thereof was 0.02 ppm by weight which is the detection limit or less.

TABLE 1

| (Ion chromatograph measurement conditions) | |
|---|---|
| Apparatus | DIONEX DX-500 |
| Column | AG11 + AS11 |
| Thermostat bath temperature | 35° C. |
| Flow rate of eluent | 2 ml/min |
| Eluent | NaOH aqueous solution (0.1 mmol/liter) |
| Detector | Electric conductivity type detection |

Example 1

Tetrachloroethylene was added to the above commercially available 1-hexene (a product of Mitsubishi Chemical Corporation, Dialen 6), and concentration was adjusted to 1 ppm by weight as a concentration in terms of a chlorine atom. Such a solution was used as 1-hexene for linear low density polyethylene (LLDPE) production raw material.

The inside of a 2.4 liters (inner volume) stirring type autoclave equipped with a rupture disk therein was thoroughly substituted with nitrogen, and 0.5 liter of special grade toluene (a product of Wako Pure Chemical Industries, Ltd., a special grade reagent is passed through a molecular sieve (MS) packed column to remove water) was introduced therein. The rupture disk is used to contact a specific catalyst component under polymerization atmosphere.

1.8 ml of a heptane solution of triisobutylaluminum (0.1 mmol-Al/ml heptane; heptane used is the same purified heptane as above) was added to toluene in the autoclave, and subsequently, 3.4 ml of a toluene solution of triphenylmethyl tetrakispentafluorophenyl borate (0.62 µmol/ml; toluene is one obtained by passing a special grade reagent, a product of Wako Pure Chemical Industries, Ltd., through an MS packed column to remove water) was added. Furthermore, 100 ml of the above raw material 1-hexene was added.

On the other hand, 1.4 ml of a toluene solution of dimethylsilylene bis(4,5,6,7-tetrahydroindenyl)zirconium dichloride (1.0 µmol/ml; toluene used is the same purified toluene as above) was added to the rupture disk side. Inner pressure of the autoclave was purged. Thereafter, the temperature in the autoclave was elevated to 85° C., and the rupture disk was ruptured by ethylene pressure. Ethylene partial pressure in the autoclave was controlled to be 0.1 MPa, and polymerization was conducted at 85° C. for 0.5 hour. The yield of a polymer (linear low density polyethylene (LLDPE)) obtained by polymerization is shown in Table 2.

Example 2

The same operation as in Example 1 was conducted except for using cis-1,2-dicholroethylene in place of tetrachloroethylene. The yield of a polymer (linear low density polyethylene (LLDPE)) obtained is shown in Table 2.

Comparative Example 1

Polymerization was conducted by operating in the same manner as in Example 1 except for directly using the above commercially available 1-hexene (a product of Mitsubishi Chemical Corporation, Dialen 6) as a raw material for linear low density polyethylene production. The yield of a polymer (linear low density polyethylene (LLDPE)) obtained is shown in Table 2.

TABLE 2

| | Kind of organohalide in 1-hexene | | |
|---|---|---|---|
| | Kind | Concentration (in term of halogen atom) | LLDPE yield |
| Example 1 | Tetrachloroethylene | 1 ppm by weight | 97 g |
| Example 2 | 1,2-Dichloroethylene (cis-form) | 1 ppm by weight | 89 g |
| Comparative Example 1 | — | 0 ppm by weight | 66 g |

It is seen from Examples 1 and 2 and Comparative Example 1 that when (a linear low density polyethylene (LLDPE)) is produced using 1-hexene in which concentration of an organohalide to 1-hexene as a raw material is from 0.05 to 10 ppm by weight in terms of a halogen atom, activity of a catalyst for polymer production is improved, and the yield is increased.

Example 3

Tetrachloroethylene was added to the above commercially available 1-hexene (a product of Mitsubishi Chemical Corporation, Dialen 6), and concentration was adjusted to 1 ppm by weight as a concentration in terms of a chlorine atom. Such a solution was used as 1-hexene for a raw material of linear low density polyethylene (LLDPE) production.

The inside of a 2.4 liters (inner volume) stirring type autoclave equipped with a rupture disk therein was thoroughly substituted with nitrogen, and 0.5 liter of special grade toluene (a product of Wako Pure Chemical Industries, Ltd., a special grade reagent is passed through a molecular sieve (MS) packed column to remove water) was introduced therein. The rupture disk is used to contact a specific catalyst component under polymerization atmosphere.

1.8 ml of a heptane solution of triisobutylaluminum (0.1 mmol-Al/ml heptane; heptane used is the same purified heptane as above) was added to toluene in the autoclave, and subsequently, 3.4 ml of a toluene solution of triphenylmethyl tetrakispentafluorophenyl borate (0.62 µmol/ml; toluene is one obtained by passing special grade toluene, a product of Wako Pure Chemical Industries, Ltd., through an MS packed column to remove water) was added. Furthermore, 20 ml of the above raw material 1-hexene was added.

On the other hand, 1.4 ml of a toluene solution of bis (normal butylcyclopentadienyl)hafnium dichloride (1.0 µmol/ml; toluene used is the same purified toluene as above) was added to the rupture disk side. Inner pressure of the autoclave was purged. Thereafter, the temperature in the autoclave was elevated to 85° C., and the rupture disk was ruptured by ethylene pressure. Ethylene partial pressure in the autoclave was controlled to be 0.2 MPa, and polymerization was conducted at 85° C. for 1.0 hour. The yield of a polymer (linear low density polyethylene (LLDPE)) obtained by polymerization is shown in Table 3.

Example 4

Polymerization was conducted by operating in the same manner as in Example 3 except that tetrachloroethylene in place of the commercially available 1-hexene was added to 1-hexene obtained in Reference Example 2 to adjust the amount of a chloride in a raw material olefin to the amount of 5 ppm by weight in terms of a chlorine atom concentration, and such a solution was used as a raw material for linear low density polyethylene (LLDPE) production. The yield of a polymer (linear low density polyethylene (LLDPE)) obtained is shown in Table 3.

Comparative Example 2

Polymerization was conducted by operating in the same manner as in Example 3 except that tetrachloroethylene in place of the commercially available 1-hexene was added to 1-hexene obtained in Reference Example 2 to adjust the amount of a chloride in a raw material olefin to the amount of 25 ppm by weight in terms of a chlorine atom concentration, and such a solution was used as a raw material for linear low density polyethylene (LLDPE) production. The yield of a polymer (linear low density polyethylene (LLDPE)) obtained is shown in Table 3.

Comparative Example 3

Polymerization was conducted by operating in the same manner as in Example 3 except for directly using the commercially available 1-hexene (a product of Mitsubishi Chemical Corporation, Dialen 6) as a raw material for linear low density polyethylene production. The yield of a polymer (linear low density polyethylene (LLDPE)) obtained is shown in Table 3.

TABLE 3

| | Kind of organohalide added to raw material 1-hexene | Amount of organohalide in raw material 1-hexene (in terms of halogen atom) | LLDPE yield |
| --- | --- | --- | --- |
| Example 3 | Tetrachloroethylene | 1 ppm by weight | 26 g |
| Example 4 | Tetrachloroethylene | 5 ppm by weight | 23 g |
| Comparative Example 2 | Tetrachloroethylene | 25 ppm by weight | 16 g |
| Comparative Example 3 | — | 0 ppm by weight | 20 g |

It is seen from Example 3 and Comparative Example 3 that when (a linear low density polyethylene (LLDPE)) is produced using 1-hexene in which concentration of an organohalide to 1-hexene as a raw material is from 0.05 to 10 ppm by weight in terms of a halogen atom, activity of a catalyst for polymer production is improved, and the yield is increased.

It is seen from Example 4 and Comparative Example 2 that when 1-hexene obtained by trimerization reaction of ethylene using a chromium series catalyst comprising a combination of the chromium compound (a), the nitrogen-containing compound (b), the aluminum-containing compound (c) and the halogen-containing compound (d) is used as a raw material 1-hexene, and the amount of a chloride contained therein is in a range of from 0.05 to 10 ppm by weight in terms of a chlorine atom, catalyst activity is improved, and the yield of a polymer (linear low density polyethylene (LLDPE)) obtained is increased. Furthermore, it is expected that even when a linear low density polyethylene (LLDPE) is produced using 1-hexene continuously produced as in Reference Example 1 as a raw material, the same effect is exhibited.

While the invention has been described in detail and with reference to the specific embodiments thereof, it will be apparent to one skilled in the art that various changes and modifications can be made therein without departing from the spirit and scope thereof.

This application is based on Japanese Patent Application (Patent Application No. 2006-351967) filed Dec. 27, 2006, the entire contents thereof being hereby incorporated by reference.

INDUSTRIAL APPLICABILITY

According to the present invention, catalyst activity is increased, and a polyolefin such as a linear low density polyethylene can industrially advantageously be produced. Therefore, the industrial value of the present invention is remarkable.

The invention claimed is:

1. A production method comprising producing a polyolefin by polymerization reaction of a raw material olefin in the presence of a single-site catalyst, wherein the concentration of an organohalide to the raw material olefin is from 0.05 to 10 ppm by weight in terms of a halogen atom, wherein the organohalide is a halogenated olefin.

2. The production method as claimed in claim 1, wherein 1-hexene is used as the raw material olefin.

3. The production method as claimed in claim 2, wherein the 1-hexene is obtained by trimerization reaction of ethylene using a chromium series catalyst comprising a combination of a chromium compound (a), a nitrogen-containing compound (b), an aluminum-containing compound (c) and a halogen-containing compound (d).

4. A polyolefin, which comprises an organohalide in an amount of from 0.005 to 1 ppm by weight in terms of a halogen atom, wherein the organohalide is a halogenated olefin.

5. The polyolefin as claimed in claim 4, which is a linear low density polyethylene.

6. A composition comprising 1-hexene and, based on the amount of 1-hexene, a halogenated olefin selected from the group consisting of monochloroethylene, 1,1-dichloroethylene, 1,2-dichloroethylene (cis- and trans-forms), trichloroethylene, and tetrachloroethylene, in an amount of from 0.05 to 10 ppm by weight in terms of a halogen atom.

7. The composition as claimed in claim 6, wherein the 1-hexene is obtained by trimerization reaction of ethylene using a chromium series catalyst comprising a combination of a chromium compound (a), a nitrogen-containing compound (b), an aluminum-containing compound (c) and a halogen-containing compound (d).

8. The production method as claimed in claim 2, wherein said concentration is from 0.1 to 10 ppm by weight.

9. The production method as claimed in claim 2, wherein said concentration is from 0.5 to 10 ppm by weight.

10. The polyolefin as claimed in claim 4, wherein said amount is from 0.005 to 0.5 ppm by weight.

11. The production method as claimed in claim 1, wherein the halogenated olefin is selected from the group consisting of monochloroethylene, 1,1-dichloroethylene, 1,2-dichloroethylene (cis- and trans-forms), trichloro-ethylene, and tetrachloroethylene.

12. The polyolefin as claimed in claim 5, wherein the linear low density polyethylene is obtained from a composition comprising 1-hexene and, based on the amount of 1-hexene, the halogenated olefin in an amount of from 0.05 to 10 ppm by weight in terms of a halogen atom.

13. The polyolefin as claimed in claim 12, wherein the halogenated olefin is selected from the group consisting of monochloroethylene, 1,1-dichloroethylene, 1,2-dichloroethylene (cis- and trans-forms), trichloro-ethylene, and tetrachloroethylene.

* * * * *